United States Patent [19]

Uesu et al.

[11] Patent Number: 5,303,032
[45] Date of Patent: Apr. 12, 1994

[54] METHOD OF MEASURING THE TIME FOR FORMING REFRACTIVE INDEX GRATING OF A PHOTO-NONLINEAR MEDIUM

[75] Inventors: Yoshiaki Uesu; Jun Iba; Toshiyuki Yoshihara, all of Tokyo; Kazuyasu Hikita; Hiroyuki Iizuka, both of Saitama, all of Japan

[73] Assignee: Mitsubishi Materials Corporation, Tokyo, Japan

[21] Appl. No.: 949,392

[22] Filed: Sep. 22, 1992

[30] Foreign Application Priority Data

Mar. 19, 1992 [JP] Japan .................................. 4-93546

[51] Int. Cl.$^5$ .............................................. G01B 9/02
[52] U.S. Cl. .................................. 356/345; 356/347; 359/300
[58] Field of Search ............... 356/345, 347, 348, 354, 356/355; 359/300

[56] References Cited

U.S. PATENT DOCUMENTS 4,453,803  6/1984  Ashkin et al. ...................... 359/300

OTHER PUBLICATIONS

"New Optical Gyroscope Based on the Passing Phase Conjugation", Fischer et al, Applied Physics Letters, Jul. 1985, pp. 1–3.
"Phase Conjugate Mirrors", Gowen, SPIE Symposium 84, Apr. 1984.

Primary Examiner—Samuel A. Turner
Attorney, Agent, or Firm—McAulay Fisher Nissen Goldberg & Kiel

[57] ABSTRACT

A laser beam with a wavelength λ emitted from a laser beam source is split into first and second pump beams and a probe beam. The first and second pump beams are incident on light incident surfaces of a photo-nonlinear medium from opposing directions on the same optical path. The probe beam is incident on the light incident surface forming an angle with the first pump beam to generate interference fringes in the normal direction of the light incident surface and to form a refractive index grating. A phase conjugate wave is emitted in the reverse direction to an incident optical path of the probe beam by means of irradiating the second pump beam on the refractive index grating. A direct-current electric field is applied on a pair of external electrodes to be coincident to the wave vector of the interference fringes, where by providing a frequency modulation to the first pump beam using a piezoelectric oscillator, a moving speed "v" of the interference fringes is determined when light intensity of the phase conjugate wave is maximized. A forming time τ of the refractive index grating can thus be obtained. An accurate and rapid measurement can generally be obtained for the forming time of the refractive index grating of the photononlinear medium formed of photorefractive crystal including a cubic system such as BSO.

5 Claims, 6 Drawing Sheets

MOVING SPEED OF INTERFERENCE FRINGES (μm/s)

METHOD OF MEASURING THE TIME FOR FORMING REFRACTIVE INDEX GRATING OF A PHOTO-NONLINEAR MEDIUM

BACKGROUND OF THE INVENTION

1. Field of the Invention

This invention relates to a four-wave mixing method for generating a phase conjugate wave by using a photorefractive effect of a photo-nonlinear medium. In particular, it relates to a method of measuring the time for forming a refractive index grating of a photo-nonlinear medium in accordance with a method of mixing four-waves.

2. Description of the Related Art

Figure 5:
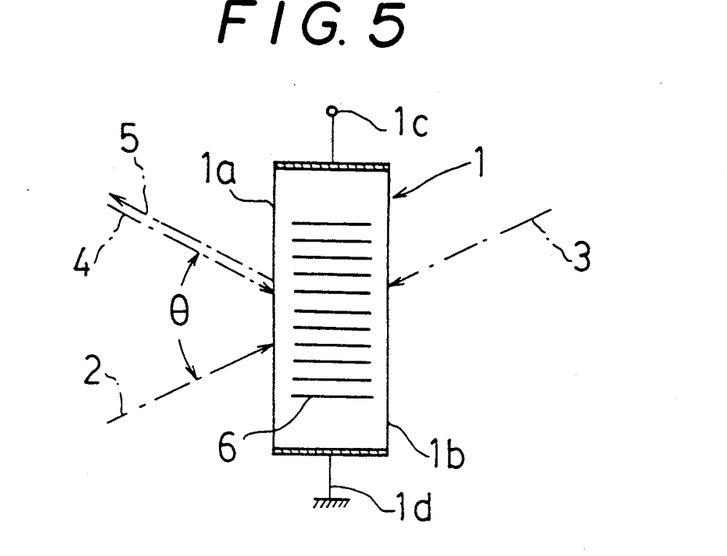
FIG. 5 is an illustrative view of a principle of generating a phase conjugate wave by a photorefractive crystal of a four-wave mixing device.

As shown in FIG. 5, a four-wave mixing device includes a photo-nonlinear medium 1 made of photorefractive crystal. Both opposing surfaces of the photo-nonlinear medium 1 are formed thereon with light incident surfaces 1a and 1b. A pair of external electrodes 1c and 1d are provided on both opposing surfaces in the orthogonal direction to the normal direction of the light incident surfaces 1a and 1b. Numerals 2 and 3 depict first and second pump beams respectively, 4 a probe beam, and 5 a phase conjugate wave generated by four-wave mixing. The probe beam 4 and the first pump beam 2 form a specified angle $\theta$ therebetween to be incident on light incident surface 1a of the photo-nonlinear medium 1; the second pump beam 3 travels on the same optical path as, and in the opposing direction to, the first pump beam 2 and is incident on light incident surface 1b.

The first pump beam 2 and probe beam 4 are incident on the light incident surface 1a of the photo-nonlinear medium 1 to produce light interference fringes in the normal direction of the light incident surface. The light interference fringes form a refractive index grating 6.

Figure 6:
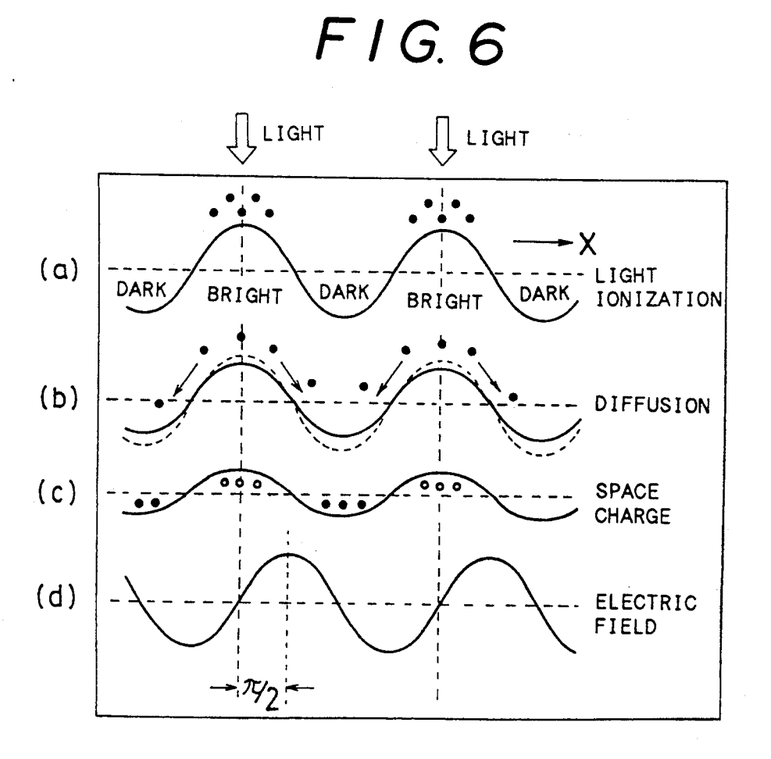
FIG. 6 is an illustrative view of a process where a refractive index grating is formed from interference fringes produced in the photo-nonlinear medium thereof.

A process of forming the refractive index grating 6 is explained in the following. In the photorefractive crystal, there is provided a level at which an impurity or the like acts as a donor or an acceptor each having electrical charges. As shown in FIG. 6(a), if a light interference between the first pump beam 2 and the probe beam 4 provides a pattern of light contrast, i.e., the interference fringes in the crystal, then electric charges, for example, electrons at a bright portion, are excited to a conducting band. When the external electric field is not applied on the crystal, the electrons are diffused in the conducting band s shown in FIG. 6(b) and trapped at the other level to reduce a space charge distribution as shown in FIG. 6(c). In such a case, the external electric field is applied through the electrodes 1c and 1d provided on the crystal. The electrons thus excited must drift to obtain a larger moving distance.

As in the foregoing arrangement, the space charge distribution produced in the crystal along the direction "x" induces a partial space electric field E, where a change of refractive index arises by Pockels effect caused by such electric field. The charge $\rho$ is satisfied by the following equation:

$$dE/dx = -\rho \quad (1)$$

In the case where the electrons are diffused to move, the refractive index grating 6 formed by the refractive index change is shifted in its phase by $\pi/2$ relative to a light intensity distribution (contrast of light). On the other hand, from the process of drifting due to the external electric field, the refractive index grating 6 and the light intensity distribution both come into phase with each other. In this way, a phenomenon where the refractive index is changed by irradiation of light on the crystal is called a photorefractive effect.

In the case where optical frequencies $\omega$ of the probe beam 4 and the pump beams 2 and 3 are made equal to each other and another coherent second pump beam 3 is incident on the refractive index grating 6 through the light incident surface 1b, then the second pump beam 3 is diffracted by the refractive index grating 6, the diffracted beam 5 travels in the reverse direction on the incident optical path of the probe beam 4. Such diffracted beam 5 is a phase conjugate wave having the same optical frequency $\omega$(phase) as those three waves of the probe beam 4 and pump beams 2 and 3, and having a relationship of being a complex conjugate with an electric field amplitude of the probe beam 4.

The phase conjugate wave 5 reversely travels exactly along the optical path followed by the probe beam 4. Accordingly, by using such characteristic, consideration is provided for various utilizations such as in a real-time hologram and an image recovery. However, in the four-wave mixing method using the photorefractive effect, a reflection factor of the phase conjugate wave is relatively low. To raise the reflection factor of the phase conjugate wave, for the four-wave mixing devices of this kind there have been proposed a moving grating method of moving the refractive index grating 6 and the interference fringes respectively in the photorefractive crystal as described in the following documents:

1. J. P. Huignard, et. al., Optics Communications 38,249 (1981),
2. N. Nuktarev, et. al., Ferroelectrics 22,949 (1979).
3. H. Rajbenback, et. al., Optics Letters, 9, 558 (1984).
4. J. P. Huignard, et. al., Appl. Optics 24, 4285 (1985).

Figure 7:
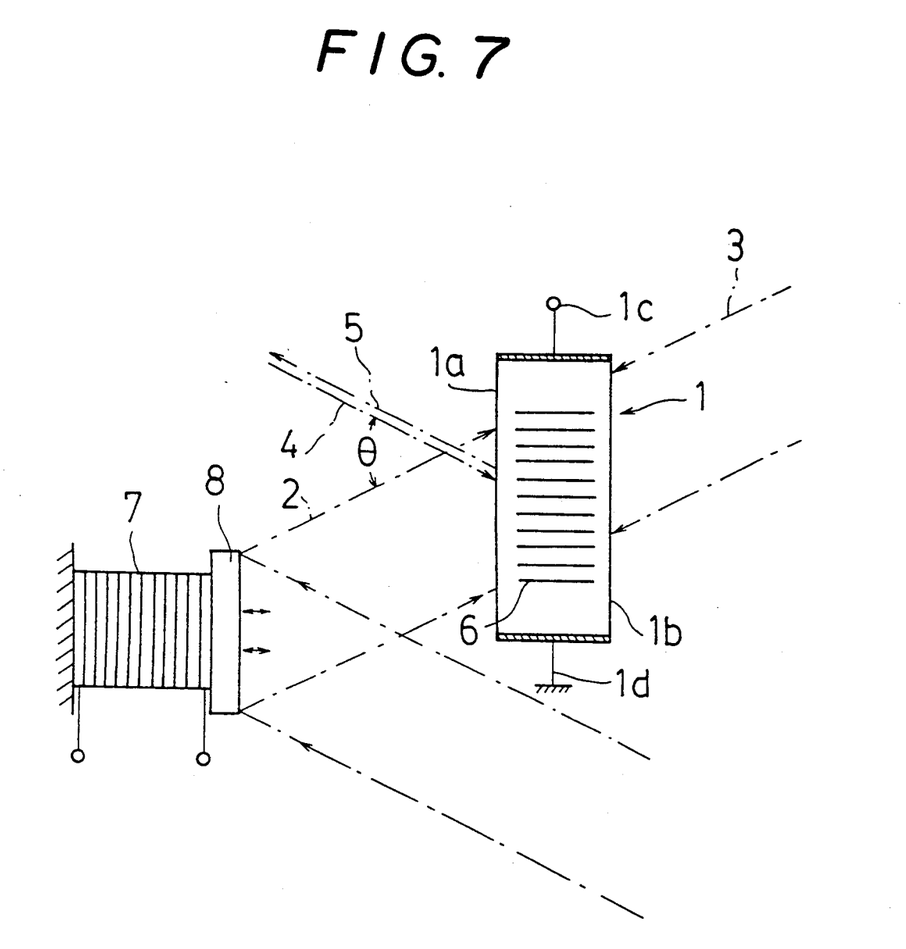
FIG. 7 is an illustrative view of a principle of generating a phase conjugate wave on the basis of a moving grating method of the four-wave mixing device.

FIG. 7 is an example of the four-wave mixing device based on the moving grating method. In FIG. 7, the same or corresponding parts as in FIG. 5 are designated by the same symbols and numerals. An optical path of the first pump beam 2 is provided with a reflection mirror 8 mounted with a piezoelectric oscillator 7. A voltage signal of sawtooth waveform is input to the piezoelectric oscillator 7 to drive the reflection mirror 8, the first pump beam 2 is then shifted (Doppler shifted) by a frequency determined depending on the sawtooth shaped waveform.

In this device, electrons excited responsive to the intensity distribution of the interference fringes produced by the first pump beam 2 and the probe beam 4 are caused to drift by a direct-current electric field applied on the electrodes 1c and 1d of the photo-nonlinear medium 1. These electrons form the refractive index grating in the crystal of the photo-nonlinear medium 1 through the space electric field and contribute to a generation of the phase conjugate wave 5. When the frequency of the first pump beam 2 is slightly modulated (Doppler shifted) by the reflection mirror 8, the interference fringes can thus be moved at a constant speed.

These interference fringes require a constant response time between the instant of starting its formation in the crystal and the instant of beginning its production of the refractive index distribution. For example, in an arrangement of a photo-nonlinear medium $Bi_{12}SiO_{20}$ (hereinafter, simply referred to as "BSO"), such response time ranges from several tens ms to several hundreds ms. Accordingly, with the interference fringes being moved at a constant speed, a phase difference has resultantly been produced because the interference fringes which have formed the refractive index grating had been moved at the time that such the refractive index grating has been made up. A moving speed of the interference fringes is determined depending on an amount of modulation of an optical frequency. Therefore, an optimum phase difference can be obtained by varying an extent of the modulation. This thus results in raising a reflection factor of the phase conjugate wave.

On the other hand, the time required for forming the refractive index grating by the interference fringes of the photo-nonlinear medium is a basically important property of matter together with density of charges, mobility, diffusion coefficient, trap density, and donor acceptor density of the photorefractive crystal. For example, to apply the photo-nonlinear medium to the real-time hologram using the four-wave mixing method and the like, the time required for forming the refractive index grating is an extremely significant parameter for determining the time required for the operating process of the real-time hologram and the speed of the photo-nonlinear device.

Conventionally, the forming time of the refractive index grating has been measured by a birefringence method using a Senaramonte method etc. Such measurement, however, requires a considerably long time because of the complicated optical system. Further, the photo-nonlinear medium with an isotropy such as BSO of a cubic system can not be applied by the birefringence method because it has no birefringence, hence a method of measuring the time for forming the refractive index grating has not yet been established.

OBJECT AND SUMMARY OF THE INVENTION

A primary object of the invention is to provide a method of, generally, accurately and rapidly measuring the time for forming a refractive index grating of a photo-nonlinear medium formed of photo-refractive crystal including the crystal of a cubic system such as BSO ($Bi_{12}SiO_{20}$).

Figure 1:
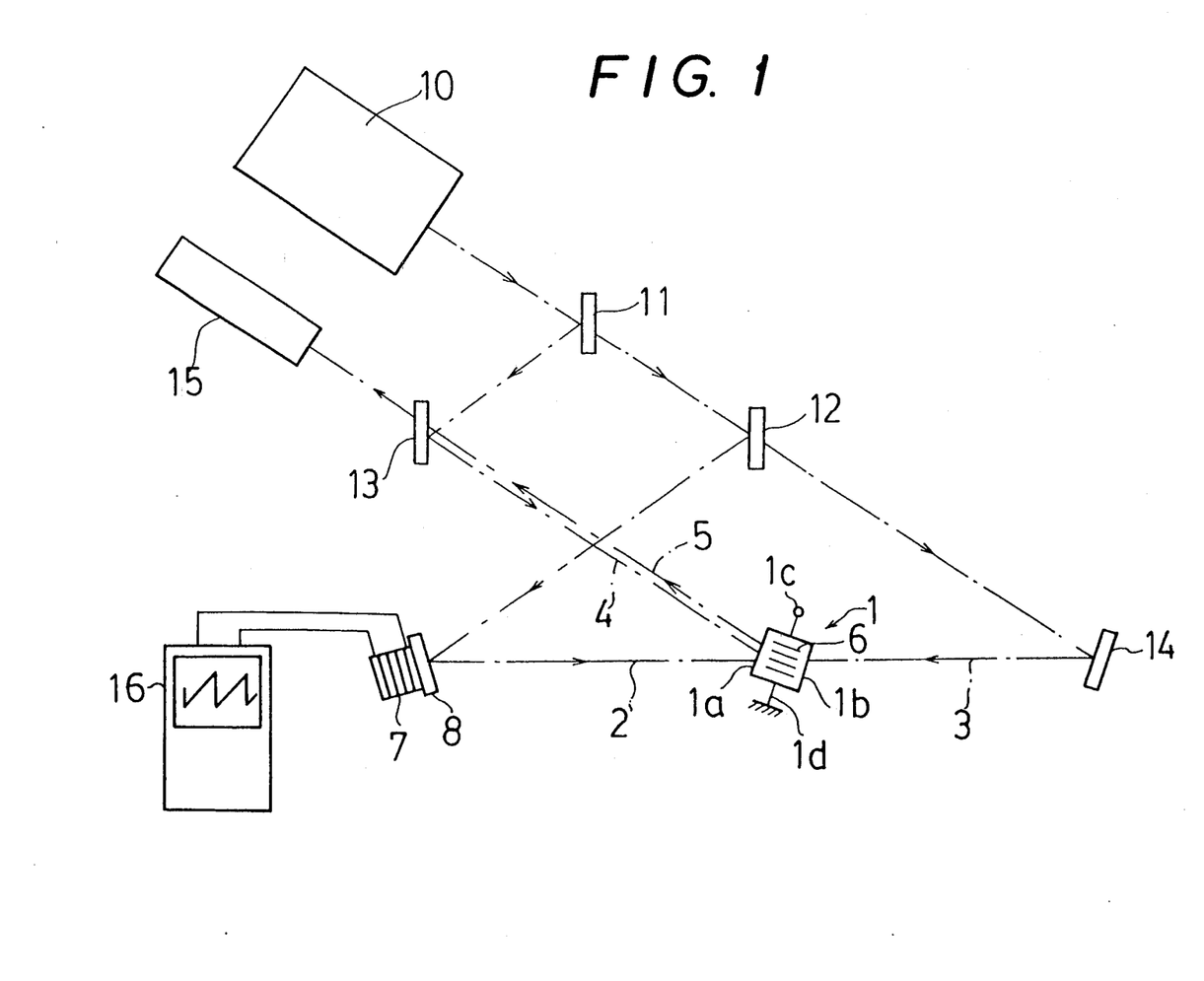
FIG. 1 is an illustrative view of a characteristic measurement device for measuring a photo-nonlinear medium using a four-wave mixing device of an embodiment according to the invention.

An inventive method of measuring the time for forming a refractive index grating of a photo-nonlinear medium is accomplished in accordance with a method of mixing four-waves as shown in FIG. 1. The method of mixing four-waves is a method wherein a laser beam with a wavelength λ emitted from a laser beam source 10 is split into first and second pump beams 2 and 3 and a probe beam 4; the first and second pump beams 2 and 3 are incident on light incident surfaces 1a and 1b from opposing directions on the same optical path, the light incident surfaces 1a and 1b being formed on both surfaces opposing each other on a photo-nonlinear medium 1; simultaneously in addition to the first pump beam 2, the probe beam 4 incident on the light incident surface 1a forming an angle θ with the pump beam 2 generates interference fringes in the normal direction of the light incident surface 1a, thereby forming a refractive index grating 6. A phase conjugate wave 5 is emitted from the photo-nonlinear medium 1 in a direction reverse to an incident optical path of the probe beam 4 by means of irradiating the second pump beam 3 on the refractive index grating 6.

The inventive method of measuring the time for forming a refractive index grating of a photo-nonlinear medium is characterized in that: a wave vector K of the interference fringes is determined by substituting each value of the wavelength λ and the angle θ into the following equation:

$$K = (4\pi \sin(\theta/2))/\lambda;$$

a direct-current electric field is applied to a pair of external electrodes 1c and 1d to be coincident to the wave vector K of the interference fringes, the pair of the external electrodes 1c and 1d being provided on both opposing surfaces of the photo-nonlinear medium 1 a direction orthogonal to the normal direction of the light incident surfaces 1a and 1b; the interference fringes is moved by providing a frequency modulation to the first pump beam 2 using a piezoelectric oscillator 7; a moving speed "v" of the interference fringes is determined when a light intensity of the phase conjugate wave 5 is maximized; and a forming time r of the refractive index grating 6 is obtained by substituting each value of the wave vector K and a moving speed "v" of interference fringes into the following equation:

$$\tau = 1/(K \cdot v).$$

For a better understanding of the present invention, reference is made to the following description and accompanying drawings while the scope of the invention will be pointed out in the appended claims.

DESCRIPTION OF THE PREFERRED EMBODIMENTS

For a photo-nonlinear medium according to the invention there can be cited crystal having a photorefractive effect such as those of $LiNbO_3$, $LiTaO_3$, $BaTiO_3$, $Ba_2NaNb_5O_{15}$ or BSO, BGO ($Bi_{12}GeO_{20}$), BTO ($Bi_{12}TiO_{20}$) and the like.

For a beam supply source for pump beams 2 and 3 and a probe beam 4 a laser beam source 10 can be used such as an argon laser (wavelength λ=514.5 nm), a krypton laser (wavelength λ=568 nm, 647.1 nm), a ruby laser (wavelength λ=694.3 nm) or the like.

A voltage signal with a sawtooth shaped waveform is input to a piezoelectric oscillator 7 to drive a reflection mirror 8, then a first pump beam 2 is modulated (Doppler shifted) by as much as a frequency determined depending on the sawtooth waveform, interference fringes can thus be moved at a constant speed. A light intensity of a phase conjugate wave 5 produced from an incident light of a second pump beam 3 is detected by a photo intensity detector 15 to obtain therefrom a moving speed of the interference fringes capable of producing a maximum light intensity, the time required for forming a refractive index grating 6 is thus determined.

A moving speed vp of the foregoing piezoelectric oscillator is satisfied by the following equation, $$vp = x \cdot f \cdot V \quad (2)$$

where V and "f" represent an amplitude and a frequency each of a voltage applied to the piezoelectric oscillator respectively, "x" represents a coefficient of displacement. The equation of a moving speed "v" of the interference fringes is established as follows:

$$v = vp \cos \phi / (2 \sin (\theta/2)) \quad (3)$$

where $\phi$ represents an angle formed by an incident light to the reflection mirror with a normal, and angle $\theta$ is theoretically within a range as $0 \leq \theta 180$ degrees. A wave vector K of the interference fringes is produced by the following equation, $$K = (4\pi \sin (\theta/2))/\lambda \quad (4)$$

where $\theta$ represents an angle formed by the probe beam with the first pump beam and $\lambda$ represents wavelengths of the probe beam and the second pump beam respectively.

On the other hand, the moving speed "v" and the wave vector K of each of the interference fringes, and the forming time $\tau$ of the refractive index grating, are in the following relationship, $$K \cdot v \cdot \tau = 1 \quad (5)$$

therefore the forming time $\tau$ of the refractive index grating is expressed by the following equation, $$\tau = 1/(K \cdot v) \quad (6)$$

an optimum moving speed of the interference fringes (fringe velocity) obtained from the equation (3) is substituted in "v", and a value obtained from the equation (4) is substituted in K respectively, then the forming time $\tau$ of the refractive index grating can be obtained.

EXAMPLE

Figure 2:
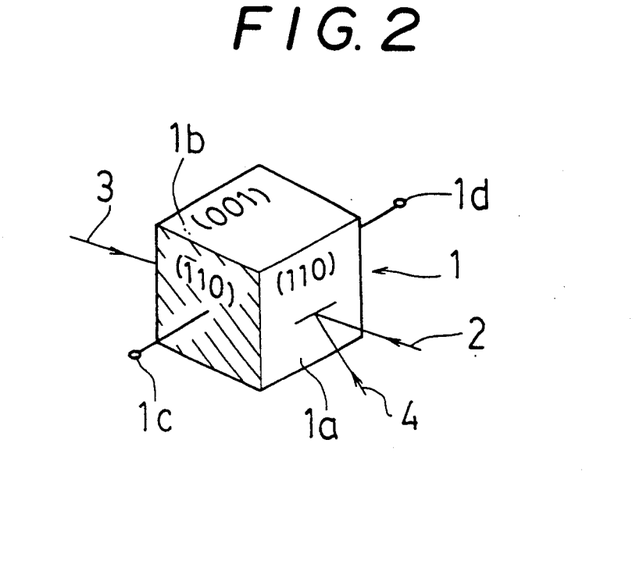
FIG. 2 is a perspective view of the photo-nonlinear medium.

An Example according to the invention will now be described in detail with reference to the drawings. In FIGS. 1 and 2, the same or corresponding parts as in FIG. 7 are designated by the same symbols or numerals. A laser beam source 10 is an argon laser with a wavelength $\lambda$ of 514.5 nm capable of continuously oscillating. The photo-nonlinear medium 1 is a cube-shaped BSO ($Bi_{12}SiO_{20}$) with each side being of 1 cm. As shown in FIG. 2, external electrodes 1a and 1b are formed by applying a thermosetting Ag paste to both surfaces having Miller indices (110) with a cubic system. Surfaces (110) are provided with the incident surfaces 1a and 1b. Numerals 11, 12, and 13 depict beam splitters, 14 a reflection mirror, and 15 a photo intensity detector for detecting a photo intensity of the phase conjugate wave 5 emitted from the photo-nonlinear medium 1. The reflection mirror 8 provided with the piezoelectric oscillator 7 is illustratively obliquely placed in the drawing, but in actual operation, the reflection mirror 8 is arranged with a reflecting surface being placed in horizontal position so as to exhibit a stable operation with respect to the reflection mirror 8. A sawtooth voltage signal is applied to the piezoelectric oscillator 7 from an oscillator 16, a direct-current electric field of 5 kV/cm is applied to the external electrodes 1c and 1d of the photo-nonlinear medium 1 to be coincident to a wave vector K of interference fringes.

A light radiated from the laser beam source 10 is incident on the incident surface 1a as a pump beam 2 through the beam splitter 12 and the reflection mirror 8. Further, the light radiated from the laser beam source 10 is incident on the incident surface 1b as a pump beam 3 through the reflection mirror 14. The pump beams 2 and 3 are incident on the light incident surfaces 1a and 1b traveling on the same optical path but respectively from the opposing directions. Further, the light radiated from the laser beam source 10 is incident on the incident surface 1a as a probe beam 4 through the beam splitters 11 and 13. An angle of $\theta$ formed by the pump beam 2 with the probe beam 4 is set to five degrees.

Each of the first pump beam 2 and the second pump beam 3 is allowed to have an optical path with a length equal to each other, but the probe beam 4 is allowed to have an optical path with a different distance from the foregoing two optical paths; in this way, by utilizing that a distance capable of interference of the argon laser is short (about 10 cm), only the first pump beam 2 and the probe beam 4 come to interfere each other. A diffracted beam 5 diffracted from the pump beam 3 by the refractive index grating 6 travels in the reverse direction on an incident optical path of the probe beam 4 as a phase conjugate wave. In this Example, the equation of a light intensity ratio is as follows:

$$E_1:E_2:E_3 = 2:1:1$$

where $E_1$, $E_2$, and $E_3$ represent light intensities of the first pump beam 2, second pump beam 3, and probe beam 4 respectively. A power density before incident on the photo-nonlinear medium 1 of the pump beam 2 is equal to 11.8 mW/cm².

In a four-wave mixing device with a construction described above, a rise time of a sawtooth voltage applied to the piezoelectric oscillator 7 is set sufficiently longer than the forming time of the refractive index grating of the photo-nonlinear medium 1, and a fall time of the same is set sufficiently shorter than the forming time of the foregoing refractive index grating. The reflection mirror 8 is displaced proportional to the sawtooth voltage to provide a frequency modulation to the first pump beam 2. Thus, the interference fringes within the photo-nonlinear medium 1 move at a constant speed. The diffracted beam 5 has its intensity changed depending on a moving speed of the interference fringes.

Figure 3:
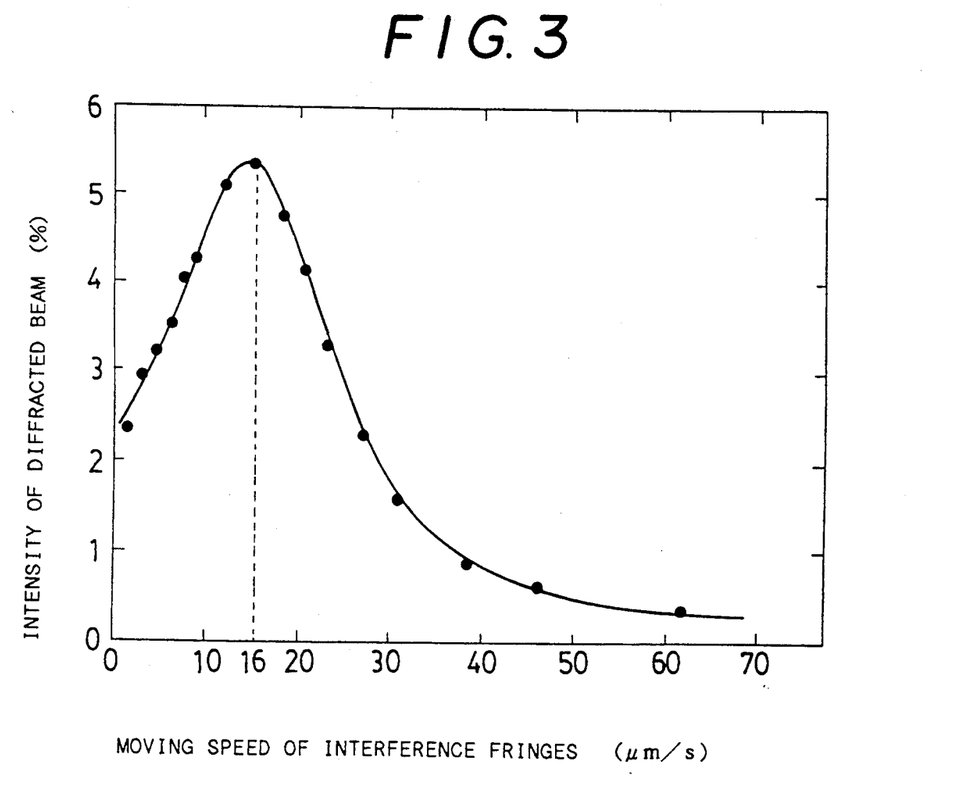
FIG. 3 is a characteristic curve of an intensity of a diffracted beam relative to a moving speed of interference fringes thereof.

FIG. 3 illustrates a measurement result of an intensity of the diffracted beam relative to a moving speed of the interference fringes. As is apparent from FIG. 3, a moving speed of the interference fringes "v" maximizing an intensity of the diffracted beam is equal to 16 $\mu$m/sec.

Algebraic numbers λ and θ in the equation (4) are substituted by 514.5 nm and by 5 degrees respectively, then a wave vector K is about $1 \times 10^6$ [l/m]. This K and v=16 μm/sec are substituted in the equation (6), then the forming time τ of the refractive index grating is obtained as 60 ms.

Figure 4:
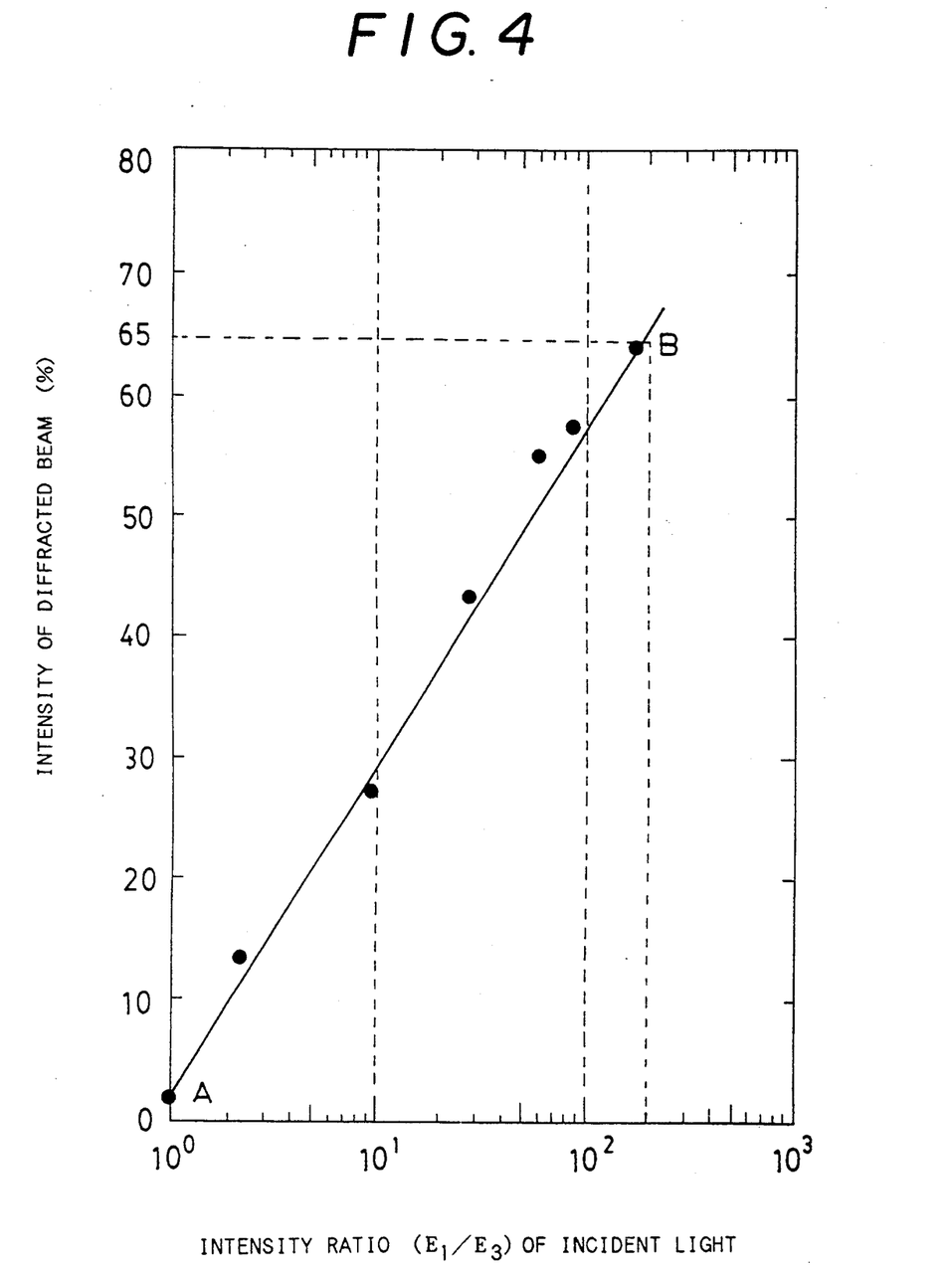
FIG. 4 is a characteristic curve of an intensity of a diffracted beam relative to an intensity ratio (E1/E3) of an incident light thereof.

In the intensity ratio of the incident light as $E_1:E_2:E_3 = 2:1:1$ ($E_1/E_3 = 2$), only $E_3$ of the probe beam is weakened to produce about $E_1/E_3 = 200$; then as shown in FIG. 4, the intensity of the diffracted beam is considerably increased from 1to 2% (A point) to about 65% (B point), obtaining the reflectivity as high as 30 to 60 times than primarily.

Figure 8:
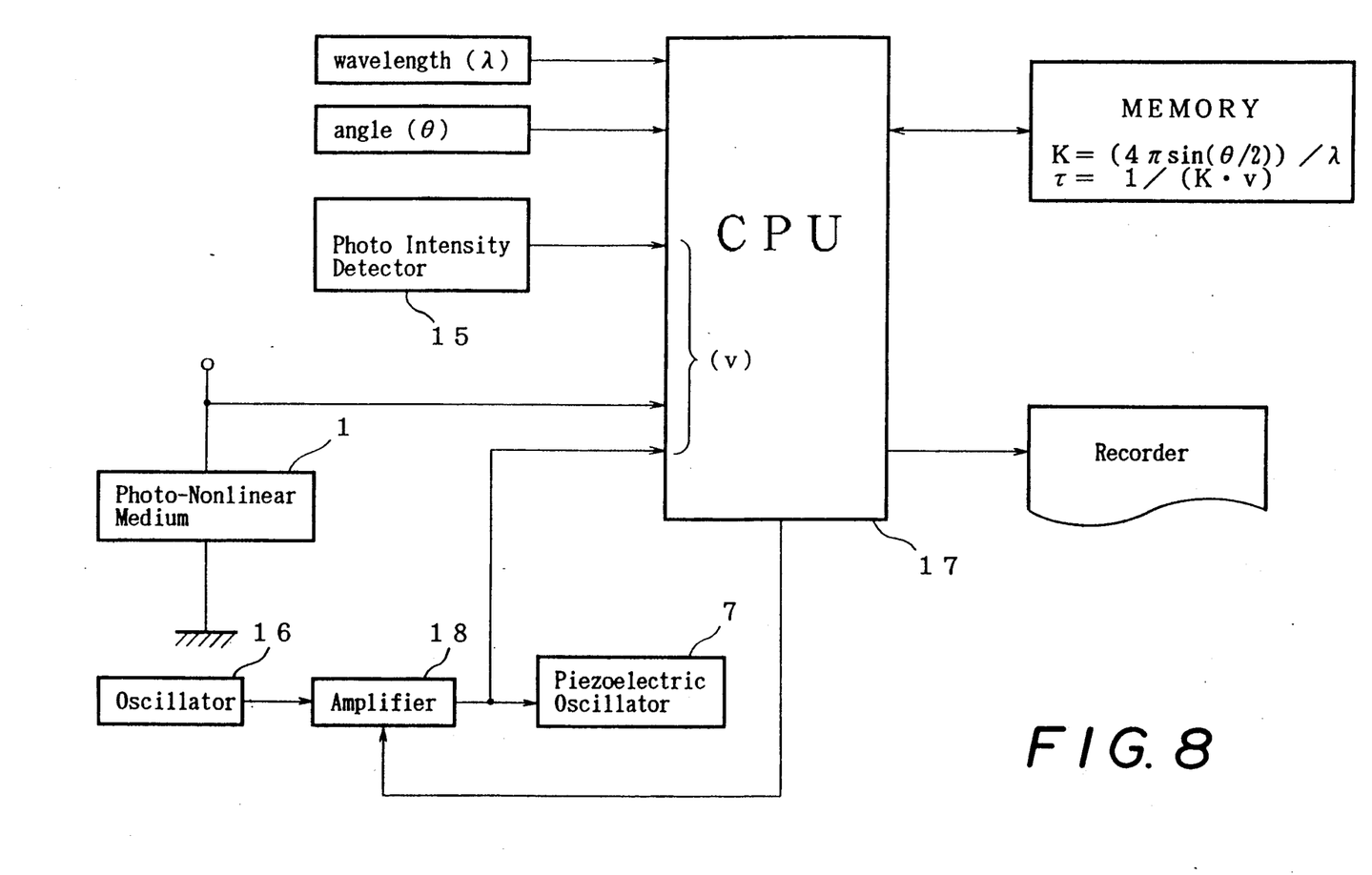
FIG. 8 is a block diagram of a computer arrangement for effecting certain computations in accordance with the present invention.

FIG. 8 illustrates in block form a generalized approach for performing the necessary calculations of the present invention by a properly programmed computer, CPU 17. The necessary parameters for determining the moving speed "v" of the interference fringes are provided to CPU 17, i.e., from amplifier 18, from the photo-nonlinear medium 1 and from the photo intensity detector 15. Also, wavelength λ and angle θ are supplied to CPU 17 to compute wave vector K which is stored in memory. From "v" and "K", the forming time τ is calculated and stored.

The values of wavelength (λ) and the angle θ may be input by manual operation or as programmed computer data. The value of the moving speed (v) of the interference fringes when a light intensity of the phase conjugate wave is maximized may be determined from the computer data according to the applied voltages of the photo-nonlinear medium 1 and piezoelectric oscillator 7 and the output of the photo intensity detector 15. Amplifier 18 is controlled by the CPU so as to move the interference fringes within the photo-nonlinear medium at a constant speed.

As hereinbefore fully described, unlike the conventional example where the forming time of the refractive index grating has been measured by a static birefringence method; according to the invention the time required for forming the refractive index grating, in general, can accurately and rapidly be measured from an optimum moving speed of the interference fringes capable of obtaining the maximum intensity by means of moving the interference fringes in the crystal at an optimum speed by modulating to a certain extent a frequency of the first pump beam using the reflection mirror with the piezoelectric oscillator.

According to invention, a measurement can also be available for the forming time of the refractive index grating of the photo-nonlinear medium of cubic system which has been unavailable in the conventional birefringence method.

The forming time of the refractive index grating for all kinds of the photo-nonlinear mediums can be measured by optionally using values of amplitude and frequency of the sawtooth voltage applied on the piezoelectric oscillator.

While the foregoing description and drawings represent the preferred embodiments of the present invention, it will be obvious to those skilled in the art that various changes and modifications may be made therein without departing from the true spirit and scope of the present invention.

What is claimed is:

1. In a method of measuring the time for forming a refractive index grating of a photo-nonlinear medium using a method of mixing four-waves including the steps of:

splitting a laser beam with a wavelength (λ) emitted from a laser beam source into first and second pump beams and a probe beam;

allowing the first and second pump beams to be correspondingly incident on first and second light incident surfaces from opposing directions on the same optical path, the first and second light incident surfaces being opposing surfaces formed on a photo-nonlinear medium;

in addition to the first pump beam, allowing the probe beam incident on the first light incident surface forming an angle (θ) with the pump beam to generate interference fringes in the normal direction of the first light incident surface, thereby forming a refractive index grating; and emitting a phase conjugate wave from the photo-nonlinear medium in a direction reverse to an incident optical path of the probe beam by means of irradiating the second pump beam on the refractive index grating, the improvement comprising the steps of:

determining a wave vector (K) of the interference fringes from each value of the wavelength (λ) and the angle (θ) by the following relationship:

$K = (4\pi \sin(\theta/2))/\lambda$;

applying a direct-current electric field to a pair of external electrodes to be coincident to the wave vector (K) of the interference fringes, the pair of the external electrodes provided on opposing surfaces of the photo-nonlinear medium in a direction orthogonal to the normal direction of the first and second light incident surfaces;

moving the interference fringes by providing a frequency modulation to the first pump beam using a piezoelectric oscillator;

determining a moving speed (v) of the interference fringes when light intensity of the phase conjugate wave is maximized; and determining a forming time (τ) of the refractive index grating from each value of the wave vector (K) and a moving speed (v) of the interference fringes by the following relationship:

$\tau = 1/(K \cdot v)$.

2. In apparatus for measuring the time for forming a refractive index grating of a photo non-linear medium by mixing four waves, said apparatus having means for splitting a laser beam with a wavelength (λ) emitted from a laser beam source into first and second pump beams and a probe beam, means for directing the first and second pump beams to be incident on first and second light incident surfaces of said photo-nonlinear medium from opposing directions on the same optical path, the first and second light incident surfaces being opposing surfaces of said medium; means for directing the probe beam to be incident on the first light incident surface so as to form an angle (θ) with the pump beam to generate interference fringes in the normal direction of the first light incident surface, thereby forming a refractive index grating; said photo non-linear medium emitting a phase conjugate wave in a direction reverse to the incident optical path of the probe beam by irradiation of the second pump beam on the refractive index grating, the improvement comprising:

means for determining a wave vector (K) from each value of the wavelength (λ) and the angle (θ) by the following relationship:

$$K = (4\pi \sin(\theta/2))/\lambda;$$

means for applying a direct-current electric field to a pair of external electrodes to be coincident to the wave vector (K) of the interference things, said external electrodes being provided on opposing surfaces of the photo-nonlinear medium in a direction orthogonal to the normal direction of the first and second light incident surfaces;

means for moving the interference fringes, said means providing frequency modulation to the first pump beam;

means for determining a moving speed (v) of the interference fringes when light intensity of the conjugate wave is maximized; and means for determining a forming time (τ) of the refractive index grating from each value of the wave vector (K) and a moving speed (v) of the interference fringes by the following relationship:

$$\tau = 1/(K \cdot v).$$

3. The apparatus of claim 2 wherein said means for moving the interference fringes includes a piezoelectric oscillator for applying frequency modulation to the first pump beam by movement of a reflecting mirror in the path of said beam.

4. The apparatus of claim 3 wherein a sawtooth voltage is applied to the piezoelectric oscillator having a rise time longer than the forming time of the refractive index grating and a fall time shorter than the forming time of the refractive index grating.

5. The apparatus of claim 2 wherein said means for moving the interferences fringes moves said fringes at a constant speed.

* * * * *